(12) United States Patent
Matsuda et al.

(10) Patent No.: US 7,144,976 B2
(45) Date of Patent: Dec. 5, 2006

(54) COUMARIN ENDCAPPED ABSORBABLE POLYMERS

(75) Inventors: Takehisa Matsuda, Fukuoka (JP); Manabu Mizutani, Osaka (JP); Steven Arnold, Sparta, NJ (US)

(73) Assignee: Ethicon, Inc., Somerville, NJ (US)

( * ) Notice: Subject to any disclaimer, the term of this patent is extended or adjusted under 35 U.S.C. 154(b) by 165 days.

(21) Appl. No.: 10/140,650

(22) Filed: May 8, 2002

(65) Prior Publication Data

US 2002/0169275 A1 Nov. 14, 2002

Related U.S. Application Data

(62) Division of application No. 09/625,793, filed on Jul. 26, 2000, now Pat. No. 6,423,818.
(60) Provisional application No. 60/146,507, filed on Jul. 30, 1999, now abandoned.

(51) Int. Cl.
*C08G 63/08* (2006.01)
*A61F 2/00* (2006.01)

(52) U.S. Cl. .................. 528/354; 528/355; 528/357; 528/359; 528/361; 528/363; 128/898; 523/111; 523/113; 523/124; 523/125; 522/1; 522/6; 522/71; 427/2.1; 427/2.31; 427/457; 427/461; 427/468; 427/553; 427/558; 427/384; 427/487; 427/493; 525/408; 525/411; 525/413; 525/415; 428/480

(58) Field of Classification Search ................ 528/354, 528/355, 357, 359, 361, 363; 128/898; 623/1.15, 623/1.46, 1.42; 522/1, 6, 71; 427/2.3, 2.31, 427/384, 457, 461, 468, 487, 493, 553, 558, 427/559; 525/408, 411, 413, 415; 523/111, 523/113, 124, 125; 428/480; 424/422, 426

See application file for complete search history.

(56) References Cited

U.S. PATENT DOCUMENTS

| 3,797,499 | A | * | 3/1974 | Schneider ................ 606/230 |
|---|---|---|---|---|
| 4,443,430 | A | | 4/1984 | Mattei et al. |
| 4,496,446 | A | * | 1/1985 | Ritter et al. ............... 522/162 |
| 4,595,713 | A | * | 6/1986 | St. John ................... 523/105 |
| 5,342,395 | A | | 8/1994 | Jarrett et al. |
| 5,410,016 | A | | 4/1995 | Hubbell et al. ............. 528/354 |
| 5,411,554 | A | | 5/1995 | Scopelianos et al. ....... 128/898 |
| 5,427,779 | A | | 6/1995 | Elsner et al. |
| 5,442,033 | A | | 8/1995 | Bezwada et al. ........... 528/354 |
| 5,468,253 | A | | 11/1995 | Bezwada et al. ........... 606/230 |
| 5,573,934 | A | | 11/1996 | Hubbell et al. ............. 435/177 |
| 5,599,852 | A | | 2/1997 | Scopelianos et al. ....... 523/105 |
| 5,631,015 | A | | 5/1997 | Bezwada et al. ........... 424/422 |
| 5,639,851 | A | * | 6/1997 | Bezwada et al. ........... 528/354 |
| 5,653,992 | A | | 8/1997 | Bezwada et al. ........... 424/426 |
| 5,688,900 | A | | 11/1997 | Cooper et al. ............. 528/301 |
| 5,707,647 | A | | 1/1998 | Dunn et al. |
| 5,713,920 | A | | 2/1998 | Bezwada et al. ............ 6/230 |
| 5,714,159 | A | | 2/1998 | Shalaby |
| 5,728,752 | A | | 3/1998 | Scopelianos et al. ....... 523/113 |
| 5,824,333 | A | | 10/1998 | Scopelianos et al. ....... 424/423 |
| 5,858,746 | A | | 1/1999 | Hubbell et al. ............. 435/177 |
| 6,024,983 | A | | 2/2000 | Tice et al. |
| 6,084,059 | A | | 7/2000 | Matsushita |
| 6,136,333 | A | * | 10/2000 | Cohn et al. ................. 424/423 |
| 6,177,095 | B1 | * | 1/2001 | Sawhney et al. ........... 424/426 |
| 6,268,222 | B1 | | 7/2001 | Chandler |
| 6,318,996 | B1 | | 11/2001 | Melikechi et al. |
| 6,413,539 | B1 | * | 7/2002 | Shalaby ..................... 424/426 |
| 6,423,818 | B1 | * | 7/2002 | Matsuda et al. ............ 528/354 |
| 6,462,169 | B1 | * | 10/2002 | Shalaby ..................... 528/354 |
| RE37,950 | E | | 12/2002 | Dunn et al. |
| 6,503,564 | B1 | | 1/2003 | Fleming et al. |
| 6,531,147 | B1 | * | 3/2003 | Sawhney et al. ........... 424/426 |
| 6,613,432 | B1 | | 9/2003 | Zamora et al. |
| 7,012,126 | B1 | * | 3/2006 | Matsuda et al. ............ 528/354 |
| 2002/0173816 | A1 | | 11/2002 | Matsuda et al. |

OTHER PUBLICATIONS

"Molecular Design of Photocurable Liquid Biodegradable Copolymers.2. Synthesis of Coumarin–Derivatized Oligo (methaerylate)s and Photocuring" by Takehisa Matsuda and Manabu Mizutani, *Macromolecules 2000*, 33, pp. 791–794, The month is not available in the date of publication.

"Molecular Design of Photocurable Liquid Biodegradable Copolymers.1. Synthesis and Photocuring Characteristics" by Takehisa Matsuda, Manabu Mitzutani, and Seven C. Arnold, *Macromolecules 2000*, 33, 795–800, The month is not available in the date of publication.

* cited by examiner

*Primary Examiner*—P. Hampton Hightower

(57) ABSTRACT

The present invention includes photocurable, liquid polymers incorporating coumarin ester endgroups into their molecular structure, which polymers are crosslinked upon irradiation with ultraviolet light by photochemically allowed [2+2] cycloaddition reactions among the chain ends, and which crosslinked polymers are useful in the preparation of medical devices, tissue engineering scaffolds, drug delivery systems and, in particular, in vivo preparation of implants in an open surgical procedure or laproscopically.

4 Claims, 3 Drawing Sheets

COUMARIN ENDCAPPED ABSORBABLE POLYMERS

This application is a divisional application of U.S. patent application Ser. No. 09/625,793, filed Jul. 26, 2000 now U.S. Pat. No. 6,423,818 which is a non-provisional application claiming priority under 35 U.S.C. 119(e) of U.S. Provisional Patent Application Ser. No. 60/146,507, filed on Jul. 30, 1999 abandoned.

FIELD OF THE INVENTION

The invention relates to photocurable, liquid absorbable polymers containing coumarin ester endgroups, medical devices containing crosslinked coatings of such polymers, and polymeric networks formed by crosslinking such polymers, including surgical implants, tissue engineering scaffolds, adhesion prevention barriers, soft tissue bulking or defect filling agents; and drug delivery vehicles.

BACKGROUND OF THE INVENTION

The field of absorbable biomaterials has been dominated by the use of purified, naturally occurring polymers such as collagen and thermoplastic polyesters based on five common lactone monomers (glycolide, L-lactide, p-dioxanone, trimethylene carbonate, and $\epsilon$-caprolactone). Homopolymers and simple copolymers of these monomers adequately met the physical and mechanical property requirements of the first absorbable sutures and meshes. Then, polymeric blends and segmented block copolymers were developed to address the need to control more precisely not only the physical and mechanical properties of the fibers, but also the in vivo breaking strength retention profile and total absorption of these materials. In general, the majority of these polymers are strong, stiff thermoplastics that are processed by injection molding, extrusion, and other common melt processing techniques.

Recently, absorbable thermoplastic elastomers have been developed to address the need in medical device development for an elastic material, e.g. U.S. Pat. Nos. 5,468,253 and 5,713,920. In addition, absorbable polymeric liquids and pastes have been developed to increase the range of physical properties exhibited by the aliphatic polyesters based on glycolide, lactide, p-dioxanone, 5,5-dimethyl-1,3-dioxan-2-one, trimethylene carbonate, and $\epsilon$-caprolactone, e.g. U.S. Pat. Nos. 5,411,554, 5,599,852, 5,631,015, 5,653, 992, 5,688,900, 5,728,752 and 5,824,333.

Hubbell et al., in U.S. Pat. Nos. 5,573,934 and 5,858,746, disclosed the use of photocurable polymers to encapsulate biological materials including drugs, proteins, and cells in a hydrogel. The hydrogel was formed from a water soluble biocompatible macromer containing at least two free radical polymerizable substituents and either a thermal or light activated free radical initiator. An example of such a photoreactive system is an acrylate ester endcapped poly (ethylene glycol) containing ethyl eosin and a tertiary amine. After a series of light activated reactions between ethyl eosin and the amine, the acrylate endgroups polymerize into short segments that result in a crosslinked polymeric network composed of poly(ethylene glycol) chains radiating outward from the acrylate oligomers. The physical and mechanical properties of the resulting hydrogel are dependent on the reproducibility of the free radical oligomerization reaction.

Hubbell et al. expanded this concept in U.S. Pat. No. 5,410,016 in the form of photocurable, segmented block copolymers composed not only of water soluble segments, such as poly(ethylene glycol), but also of segments with hydrolizable groups, in particular, with short segments of aliphatic polyesters. In this way, the resulting hydrogel breaks down into soluble units in vitro and in vivo in a controlled fashion. The photochemistry is the same and based on the free radical polymerization of acrylate and methacrylate endgroups.

Despite these developments in the field of absorbable biomaterials, there is a need for thermosetting materials, that is, materials that can be easily applied as low molecular weight compounds, and by a controlled chemical process, crosslink to form a polymeric network having physical, mechanical and biological properties determined by its components.

Thus, it is an objective of the present invention to provide a photocurable, absorbable, thermosetting polymer for use in medical applications and drug delivery.

SUMMARY OF THE INVENTION

The present invention is directed to photocurable, fluid prepolymers comprising a polymer prepared from at least one lactone monomer selected from the group consisting of $\epsilon$-caprolactone, trimethylene carbonate, glycolide, L-lactide, D-lactide, DL-lactide, p-dioxanone, 5,5-dimethyl-1,3-dioxan-2-one, 1,4-dioxepan-2-one and 1,5-dioxepan-2-one, said prepolymer being a liquid at 65° C. or at a lower temperature and comprising coumarin ester endgroups, wherein the inherent viscosity of the polymer is between about 0.05 dL/g and about 0.8 dL/g as determined in a 0.1 g/dL solution of hexafluoroisopropanol at 25° C., and wherein the polymer is crosslinked upon irradiation with ultraviolet light, and to polymeric networks, microparticles and medical devices, each formed by irradiating fluid prepolymers of the present invention. The present invention also is directed to methods of modifying a surface of a substrate, to methods of forming medical implants and to methods of repairing bony defects, each method utilizing the fluid prepolymers of the present invention. Photocuring of the fluid prepolymers can be conducted manually, for example, in an operating room by first applying the fluid prepolymer to the desired site and then irradiating the liquid with an ultraviolet light source effective to crosslink the polymer. Alternately, photocuring can be conducted automatically using a computerized instrument, e.g. a stereolithography apparatus, to make medical devices.

DETAILED DESCRIPTION OF THE INVENTION

Figure 1:
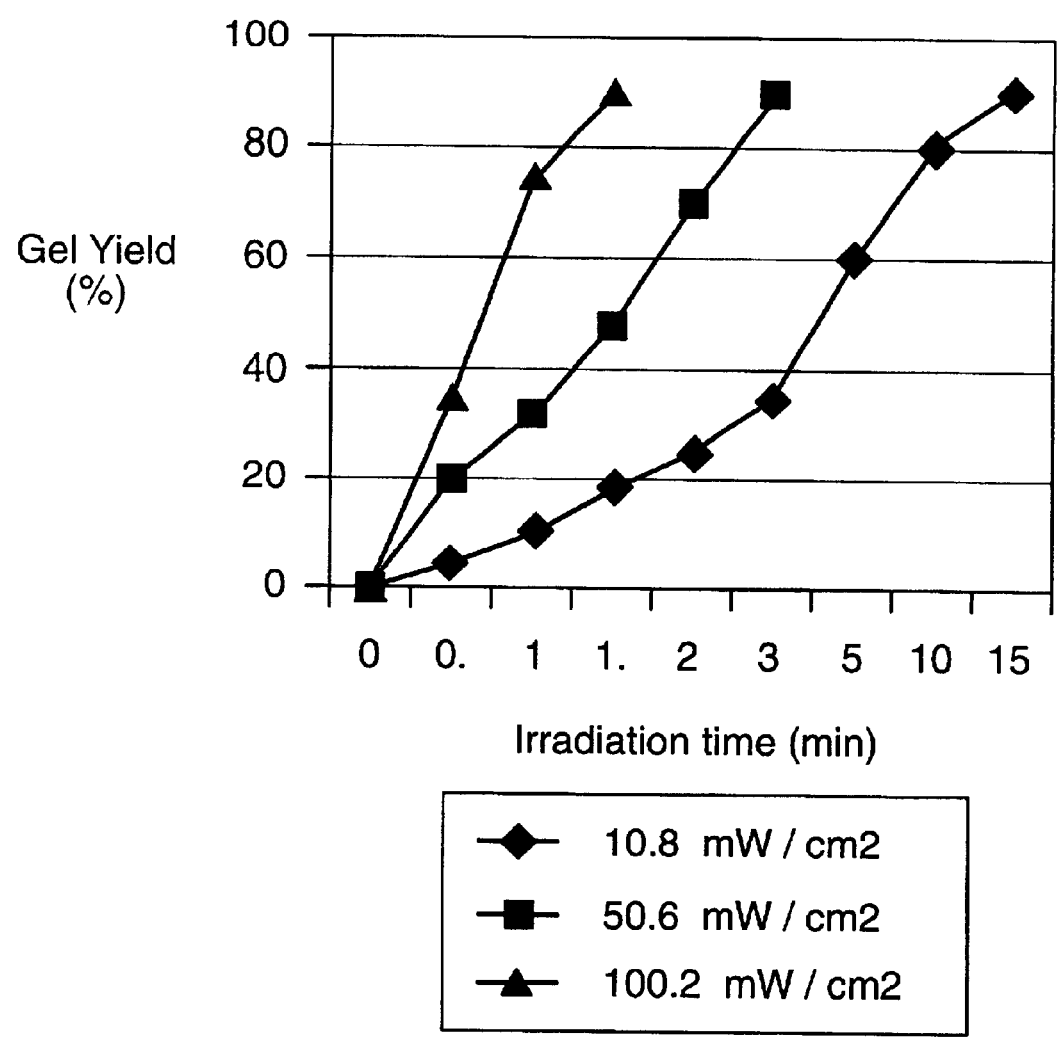
FIG. 1 is the graph plotting the % gel yield as a function of time for three ultraviolet radiation intensities for polymer E in Table 1.

The ring opening polymerization of lactone monomers has been widely studied, and the resulting aliphatic polyesters have been melt processed by extrusion and injection molding into many commercial medical devices such as sutures, suture anchors, ribbons, plates, pins, screws, rods, and staples. The most common monomers are glycolide, L-lactide, DL-lactide, p-dioxanone, 5,5-dimethyl-1,3-dioxan-2-one, trimethylene carbonate and $\epsilon$-caprolactone, and, except for poly(trimethylene carbonate) which is amorphous and above its glass transition temperature at 37° C., all of the resulting homopolymers are materials with useful physical, mechanical and biological properties. Nonetheless, there are many manufacturing processes and medical applications in which these thermoplastic polymers can not be employed because of their high viscosity, solubility or insolubility, thermal instability, crystallization kinetics, and phase separation phenomena. For these reasons and others, in the field of commodity plastics, thermosetting resins were developed. Thermosetting resins usually are prepared from low molecular weight compounds that react when mixed together or exposed to a stimulus such as heat, light, the addition of a catalyst or an initiator. Thermosetting resins typically are not melt processed, but rather are used at ambient or near ambient temperatures. The components of a thermosetting system react to form a polymeric network that exhibits excellent mechanical properties. In fact, there is excellent control of those properties by varying the type and amount of the components. In the present invention, liquid absorbable polymers made by the ring opening polymerization of lactone monomers are transformed into photocurable, thermosetting materials by an endcapping reaction that converts the hydroxyl endgroups into coumarin ester endgroups which are capable of undergoing a [2+2] cycloaddition dimerization reaction.

As disclosed in U.S. Pat. Nos. 5,411,554, 5,599,852, 5,631,015, 5,653,992, 5,728,752, and 5824,333, low molecular weight polyesters are synthesized in the same manner as high molecular weight polymers from their corresponding lactone monomers. To illustrate this, the chemical equation describing the synthesis of a liquid poly[ε-caprolactone-co-trimethylene carbonate] is shown below. $R(OH)_n$ represents a generic polyol as the initiator, $Sn(oct)_2$ represents tin (II) 2-ethyl-hexanonate as the Lewis acid catalyst, and $P(OH)_n$ represents the liquid absorbable polymer.

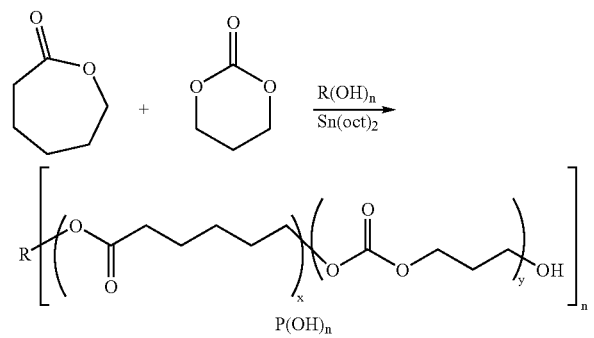

The molar ratio of the sum of the monomers in a reaction to the amount of initiator added controls the molecular weight of the resulting polymer. Consequently, the synthesis of low molecular weight, liquid absorbable polymers involves adding more initiator to the reaction than when high molecular weight materials are desired, barring any thermodynamic problems caused by a high concentration of chain ends. Branched liquid absorbable polymers can also be prepared by using multifunctional initiators such as trimethylolpropane, pentaerythritol, branched poly(ethylene glycol)s, oligomeric poly(2-hydroxyethyl methacrylate, poly(vinyl alcohol), poly(vinyl alcohol-co-vinyl acetate), or any other polyol. In fact, these multifunctional initiators can be used in conjunction with diols like ethylene glycol, 1,2-propylene glycol, 1,3-propanediol, diethylene glycol, linear poly(ethylene glycol)s, linear poly(propylene glycol)s, and linear poly(ethylene glycol-co-propylene glycol)s. Liquid absorbable polymers can be segmented block copolymers by adding different lactone monomers or different mixtures of lactone monomers sequentially to the reaction. Two or more unique liquid absorbable polymers can be mixed together and used to tailor the mixture's physical properties.

For the purposes of this invention, liquid absorbable polymer will mean any linear or branched polymer or mixture of polymers, of any possible microstructure (statistically random or segmented block), prepared from at least one lactone monomer which is a fluid at 65° C. or lower.

These liquid absorbable polymers are converted into a photocurable, thermosetting resin by converting the hydroxyl endgroups by any conceived synthetic route into a coumarin derivative. Although there are many possible endcapping reagents that could be prepared to accomplish this functionalization of the liquid absorbable polymer, the preferred endcapping agent is 7-chlorocarbonylmethoxycoumarin. The preferred synthesis of 7-chlorocarbonylmethoxycoumarin, as well as the endcapping reaction with a liquid absorbable copolymer, is shown below.

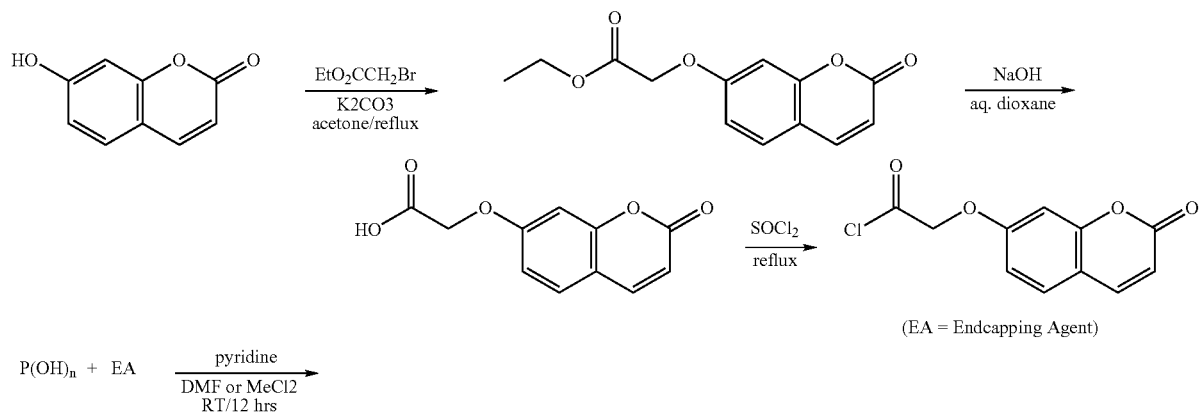

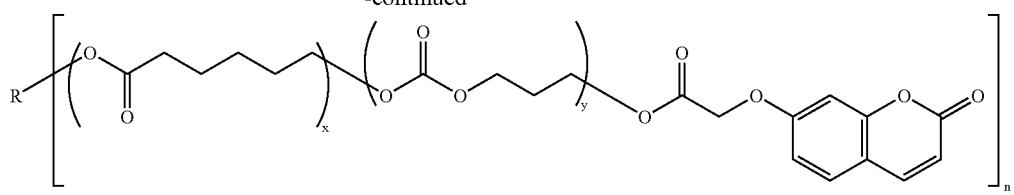

The endcapping reaction does not alter the physical state of the liquid absorbable polymer (still fluid at 65° C.) thereby providing an easy to use liquid that can be injected, pumped, spread, sprayed, or dissolved as required by the manufacturing process. When these coumarin ester endcapped, liquid absorbable polymers are irradiated with ultraviolet light, the coumarin endgroups undergo a photochemically allowed, [2+2] cycloaddition dimerization reaction as depicted below.

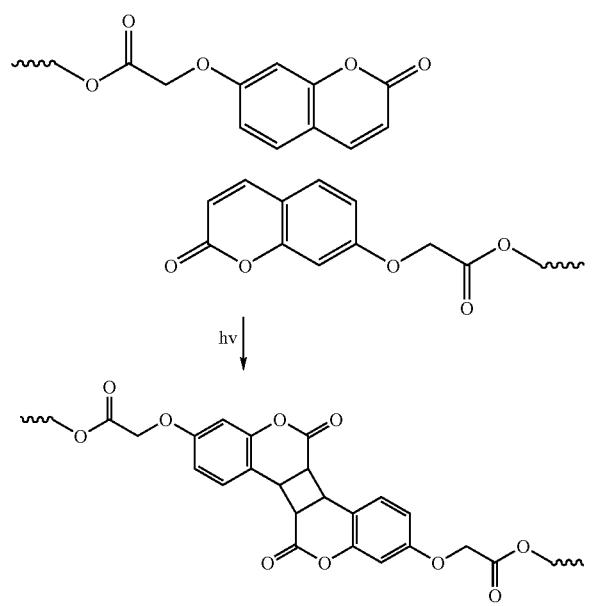

This cycloadditon reaction covalently bonds two polymers together. For a linear (difunctional) liquid absorbable polymer, the result is an increase in the molecular weight of the material. In the case when a blend of at least two compositionally different, linear, coumarin ester endcapped, liquid polymers are used, the result is the formation of a linear segmented block copolymer. For a branched (multifunctional>2) liquid absorbable polymer, the result is the formation of a polymeric network. In contrast to many other kinds of crosslinking chemistry, the coumarin dimerization reaction requires no additives, catalysts, intiators, or sensitizers which makes the system more elegant as well as safer when used in vivo.

Therefore, the present invention describes a fluid prepolymer comprising a polymer prepared from at least one lactone monomer selected from the group consisting of ε-caprolactone, trimethylene carbonate, glycolide, L-lactide, D-lactide, DL-lactide, p-dioxanone, 5,5-dimethyl-1,3-dioxan-2-one, 1,4-dioxepan-2-one and 1,5-dioxepan-2-one, said prepolymer being a liquid at 65° C. or at a lower temperature and comprising coumarin ester endgroups, wherein the inherent viscosity of the polymer is between about 0.05 dL/g and about 0.8 dL/g as determined in a 0.1 g/dL solution of hexafluoroisoproanol at 25° C., that reacts upon exposure to ultraviolet light to form a polymeric network or a segmented block copolymer depending on the overall functionality and photoconversion. The photocuring can be carried out manually, for example, in an operating room by first applying the fluid prepolymer to the desired site and then irradiating the liquid with an ultraviolet light source, or can be carried out automatically using a computerized instrument such as a stereolithography apparatus to make medical device prototypes.

In another embodiment of the present invention, a method of surface modification is disclosed comprising forming a film of the fluid prepolymer, said prepolymer comprising a polymer prepared from at least one of lactone monomer selected from the group consisting of ε-caprolactone, trimethylene carbonate, glycolide, L-lactide, D-lactide, DL-lactide, p-dioxanone, 5,5-dimethyl-1,3-dioxan-2-one, 1,4-dioxepan-2-one and 1,5-dioxepan-2-one, said prepolymer being a liquid at 65° C. or at a lower temperature and comprising coumarin ester endgroups, wherein the inherent viscosity of the polymer is between about 0.05 dL/g and about 0.8 dL/g as determined in a 0.1 g/dL solution of hexafluoroisoproanol at 25° C., on the substrate and irradiating the film with ultraviolet light effective to form a crosslinked coating. Such a coating on a medical device can be employed to modify the surface properties of the implant, thereby controlling the cellular interactions and modifying the absorption profile of absorbable devices. A template may be used to direct the ultraviolet light to only certain areas of the coated substrate. In this way, a surface architecture can be formed on the substrate akin to the photoresists of the electronics industry.

In another embodiment of the present invention, a fluid prepolymer comprising a polymer prepared from at least one lactone monomer selected from the group consisting of ε-caprolactone, trimethylene carbonate, glycolide, L-lactide, D-lactide, DL-lactide, p-dioxanone, 5,5-dimethyl-1,3-dioxan-2-one, 1,4-dioxepan-2-one, and 1,5-dioxepan-2-one, said prepolymer being a liquid at 65° C. or at a lower temperature and comprising coumarin ester endgroups, wherein the inherent viscosity of the polymer is between about 0.05 dL/g and about 0.8 dL/g as determined in a 0.1 g/dL solution of hexafluoroisoproanol at 25° C., that reacts upon exposure to ultraviolet light to form a polymeric network, and at least one bioactive compound, is disclosed for the sustained release of the entrapped drugs. Medical devices such as stents and catheters coated in this fashion become bioactive medical devices with a drug delivery component in addition to any surface modifications mentioned previously. Drug containing microparticles also can be formed by irradiating droplets of the fluid prepolymer comprising dissolved or suspended drugs and other biologically active substances.

The variety of different therapeutic agents that may be used in conjunction with the coumarin ester endcapped, liquid polymers of the invention is vast. In general, therapeutic agents which may be administered via the pharmaceutical compositions and coatings of the invention include, without limitation, anti-infectives such as antibiotics and antiviral agents, analgesics and analgesic combinations, anorexics, antihelmintics, antiarthritics, antiasthmatic agents, anticonvulsants, antidepressants, antidiuretic agents, antidiarrheals, antihistanimes, anti-inflammatory agents, antimigraine preparations, antinauseants, antineoplastics, antiparkinsonism drugs, antipruritics, antipsychotics, antipyretics, antispasmodics, anticholinergics, sympathomimetices, xanthine derivatives, cardiovascular preparations including calcium channel blockers and beta-blockers such as pindolol and antiarrhymics, antihpertensives, diuretics, vasodilators including general coronary, peripheral and cerebral, central nervous system stimulants, cough and cold preparations, including decongestants, hormones such as estradiol and other steroids including corticosteroids, hypnotics, immunosuppressives, muscle relaxants, parasympatholytics, psychostimulants, sedatives, and tranquilizers, and naturally derived or genetically engineered proteins, polysaccharides, glycoproteins, or lipoproteins. Suitable pharmaceuticals for parenteral administration are well known as is exemplified by the *Handbook on Injectable Drugs, 6th* edition, by Lawrence A Trissel, American Society of Hospital Pharmacists, Bethesda, Md., 1990 (hereby incorporated by reference).

Parenteral administration of a drug formulation of the invention can be affected by the injection of the mixture of drug and coumarin ester endcapped, liquid polymer and then photocured in situ, or by the injection of suspended, drug filled microparticles made by dissolving or mixing the drug in the coumarin ester endcapped, liquid polymer, dispersing this mixture to form small droplets, irradiating those droplets to form a crosslinked network, thereby entrapping the drug in the polymeric matrix, suspending these particles in a suitable fluid as a carrier, and then injecting that suspension into the body.

Parenteral formulations of the copolymers may be formulated by mixing one or more therapeutic agents with the liquid copolymer. The therapeutic agent may be present as a liquid, a finely divided solid, or any other appropriate physical form. Drug excipients and stabilizers may also be added to the mixture of liquid absorbable polymer and bioactive compound to produce a therapeutic product with sufficient shelf life to be safe and sold commercially.

Similar formulations can also be used in oral drug delivery formulations. In this case, the drug filled particles or solid form is placed in a capsule or is coated with a suitable barrier layer to pass through the stomach and into the intestine. Sometimes, the capsule or coating may not be necessary or desirable.

The amount of therapeutic agent will be dependent upon the particular drug employed and the medical condition being treated. Typically, the amount of drug represents about 0.001% to about 75%, more typically from about 0.001% to about 50%, and most typically from about 0.001% to about 25% by weight of the total composition.

The quantity and type of copolymers incorporated into the parenteral formulation will vary depending on the release profile desired and the amount of drug employed. For a more viscous composition, generally a higher molecular weight polymer is used. If a less viscous composition is desired, a lower molecular weight polymer can be employed. The product may contain blends of liquid copolymers to provide the desired release profile or consistency to a given formulation. In fact, the molecular weight and its distribution of the coumarin ester endcapped, liquid absorbable polymer also determines the crosslink density of the resulting polymeric network, because the individual polymer chains are simply bonded together at their ends by [2+2] cycloaddition reactions without any side reactions. The higher the initial molecular weight of the coumarin ester endcapped, liquid polymer, the longer the segment length (the number of bonds between crosslinks) of the resulting polymeric network, the lower the crosslink density. Many physical and mechanical properties like stiffness and elasticity depend on the crosslink density of the network and can be tailored by choosing the chemical composition and molecular weight the precursor liquid polymer to match the desired properties.

Individual formulations of drugs and coumarin ester endcapped, liquid absorbable polymers may be tested in appropriate in vitro and in vivo models to achieve the desired drug release profiles. For example, a drug could be formulated with the coumarin ester endcapped, liquid absorbable polymer, photocured into a coating or particles, and implanted into an animal. The drug release profile could then be monitored by appropriate means such as by taking blood samples at specific times and assaying those samples for drug concentration. Following this or similar procedures, those skilled in the art will be able to formulate a variety of sustained release parenteral formulations.

In another embodiment of the present invention, a method of forming medical implants by irradiating the fluid prepolymer, comprising a polymer prepared from at least one lactone monomer selected from the group consisting of ε-caprolactone, trimethylene carbonate, glycolide, L-lactide, D-lactide, DL-lactide, p-dioxanone, 5,5-dimethyl-1,3-dioxan-2-one, 1,4-dioxepan-2-on and 1,5-dioxepan-2-one, said prepolymer being a liquid at 65° C. or at a lower temperature and comprising coumarin ester endgroups, wherein the inherent viscosity of the polymer is between about 0.05 dL/g and about 0.8 dL/g as determined in a 0.1 g/dL solution of hexafluoroisopropanol at 25° C., in vivo is provided. In this way, polymeric networks with custom shapes are formed during surgery to prevent adhesions, to bulk tissue, or to fill tissue defects. Since the fluid prepolymer is a liquid, it can be applied to the surgical site by injection and subsequently cured by exposure to ultraviolet radiation. This series of steps may be conducted laproscopically through an appropriately design applier comprising an injection system and fiber optic light source, or more conveniently, in an open procedure with a syringe and light source.

In another embodiment of the present invention, a fluid prepolymer comprising a polymer prepared from at least one lactone monomer selected from the group consisting of ε-caprolactone, trimethylene carbonate, glycolide, L-lactide, D-lactide, DL-lactide, p-dioxanone, 5,5-dimethyl-1,3-dioxan-2-one, 1,4-dioxepan-2-one and 1,5-dioxepan-2-one, said prepolymer being a liquid at 65° C. or at a lower temperature and comprising coumarin ester endgroups, wherein the inherent viscosity of the polymer is between about 0.05 dL/g and about 0.8 dL/g as determined in a 0.1 g/dL solution of hexafluoroisopropanol at 25° C., and at least one inorganic compound, is disclosed for use as a bone filler. The number of inorganic compounds that can be used is large. The following inorganic compounds are widely used in biomedical applications and can be incorporated as components of the bone filler of this invention: alpha-tricalcium phosphate, beta-tricalcium phosphate, calcium carbonate, barium carbonate, calcium sulfate, barium sulfate, and hydroxyapatite. In this application, the ceramic or glass filled prepolymer is placed in a boney defect with or without bone fragments from the patient and then irradiated to form a temporary defect filler that will not flow out of the desired surgical site. Drugs and growth factors may also be incorporated into the formulation of fluid prepolymer and inorganic compound.

The following examples illustrate, but are not intended to limit, the scope of the claimed invention.

EXAMPLE 1
Synthesis of 7-Coumarin Ethyl Acetate Ether 20.3 grams (0.125 mol) of 7-hydroxycoumarin, 24.7 grams (0.179 mol) of potassium carbonate, 25.0 grams (0.150 mol) of ethyl bromoacetate, and 450 mL of dry acetone were added to a 500 mL round bottom flask containing a magnetic stirrer bar. The reaction mixture was stirred and refluxed for 2 hours under a $N_2$ atmosphere. The byproduct, potassium bromide, was removed by filtration, and the solvent removed by distillation on a rotary evaporator. The crude product was recrystallized from ethanol and vacuum dried. The yield was 27.7 grams (89%). $^1$H NMR (270 MHz, DMSO-$d_6$, ppm) $\delta$1.18 (3H, triplet, J=8.1 Hz), 4.16 (2H, quartet, J=8.1 Hz), 4.91 (2H, singlet), 6.28 (1H, doublet, J=9.9 Hz), 6.96 (1H, doublet, J=2.0 Hz), 6.98 (1H, quartet, J=2.0, and 8.9 Hz), 7.61 (1H, doublet, J=8.9 Hz), 7.96 (1H, doublet, J=9.9 Hz).

EXAMPLE 2
Synthesis of 7-Coumarin Acetic Acid Ether 6.92 grams (27.9 mmol) of 7-coumarin ethyl acetate ether and 280 mL of 1,4-dioxane were added to a 1 L Erlenmeyer flask containing a magnetic stirrer bar. 400 mL of water containing 16.2 grams (0.405 mol) of sodium hydroxide was added to this flask, and the mixture solution was stirred overnight at room temperature. The solution was acidified with concentrated hydrochloric acid, and organic compounds were extracted into a mixture of chloroform and methanol. These solvents were then removed by distillation under reduced pressure. The resulting crude product was recrystallized from ethanol; the yield was 5.51 grams (90%). $^1$H NMR (270 MHz, DMSO-$d_6$, ppm) $\delta$4.83 (2H, singlet), 6.28 (1H, doublet, J=9.9 Hz), 6.95 (1H, doublet, J=2.0 Hz), 6.97 (1H, doublet, J=2.0, and 8.9 Hz), 7.62 (1H, doublet, J=8.9 Hz), 7.97 (1H, doublet, J=9.9 Hz), 13.13 (1H, s).

EXAMPLE 3
Synthesis Of 7-Chlorocarbonylmethoxycoumarin 3.76 g (17.1 mmol) of 7-coumarin acetic acid ether and 20.0 mL (0.277 mol) of thionyl chloride were added to a 300 mL round bottom flask containing a magnetic stirrer bar. A water cooled condenser was attached to this flask, and the reaction mixture was stirred and refluxed for 3 hours under a $N_2$ atmosphere. The excess thionyl chloride was removed by distillation, and crude product was isolated. The yield was 4.00 grams (98%).

$^1$H NMR (270 MHz, DMSO-$d_6$, ppm) $\delta$4.83 (2H, singlet), 6.28 (1H, doublet, J=9.9 Hz), 6.94(1H, doublet, J=2.0 Hz), 6.96 (1H, quartet, J=2.0, and 8.9 Hz), 7.62 (1H, doublet, J=8.9 Hz), 7.97 (1H, doublet, J=9.9 Hz).

EXAMPLE 4
Synthesis of Poly (ε-caprolactone-co-trimethylene carbonate) P[CL/TMC]

The liquid absorbable polymers of this invention can be prepared as disclosed in U.S. Pat. Nos. 5,411,554, 5,468,253, 5,599,852, 5,631,015, 5,653,992, 5,728,752, and 5,824,333. A typical copolymerization reaction is described below. 125 μL (43 μmol) of a 0.33 M stannous 2-ethylhexanoate solution in toluene, 4.38 grams (32.6 mmol) of trimethylolpropane, 64.0 grams (0.627 mol) of recrystallized trimethylene carbonate, and 71.8 grams (0.629 mol) of vacuum distilled ε-caprolactone were transferred into a silanized, flame dried, 300 mL round bottom flask equipped with a stainless steel mechanical stirrer and a nitrogen gas blanket. The reaction flask was placed in an oil bath already set at 180° C. and held there for 8 hours. The stirrer blade was lifted out of the liquid polymer solution and replaced with an inlet adapter attached to a Firestone valve. The polymer was then devolatized under vacuum at 90° C. for 36 hours. The branched, statistically random copolymer was isolated by pouring into a glass jar. The yield was 139.0 grams (99%). Polymer E in Table 1. $M_n$=8,170 g/mol (polyethylene glycol standard; eluent, DMF). FTIR (KBr, cm$^{-1}$) 3529, 2955, 2866, 1744, 1252, 1164, and 1036. $^1$H NMR (270 MHz, CDCl$_3$, ppm) $\delta$1.37 (2H, multiplet), 1.62 (4H, multiplet), 2.01 (2H, multiplet), 2.27 (2H, multiplet), and 4.20 (6H, multiplet).

Trimethylene carbonate was recrystallized from a mixture of ethyl acetate and n-hexane. Other solvents and reagents were obtained commercially and were purified by distillation or recrystallization. $^1$H NMR spectra were measured on a JEOL JNM-GX270 FT-NMR spectrometer. The chemical shifts were given in $\delta$ values from Me$_4$Si as an internal standard. IR spectra were measured on a Shimadzu DR-8020 FT-IR spectrophotometer. UV absorption spectra were measured on a JASCO Ubest-30 UV/VIS spectrophotometer. The molecular weight of polymer was estimated by GPC analysis which was carried out on a Toso SC-8020.

EXAMPLE 5
Synthesis of Coumarin Ester Endcapped P[CL/TMC]

A typical endcapping reaction is described below. 1.05 grams (0.129 mmol) of P[CL/TMC] as prepared in Example 4, 0.427 grams (1.79 mmol) of acetyl chloride 7-coumarin as prepared in example 3, 0.050 mL (0.62 mmol) of pyridine, and 20.5 mL of dichloromethane were added to a 100 mL round bottom flask containing a magnetic stirrer bar. The reaction mixture was stirred overnight at room temperature under a $N_2$ atmosphere. The resulting coumarin ester endcapped P[CL/TMC] was isolated by precipitation in diethyl ether and purified by fractionation with DMF and 8::2 diethyl ether:methanol. The yield was 0.99 grams (86%). FTIR (KBr, cm$^{-1}$) 2953, 2866, 1743, 1614, 1250, 1164, and 1036. $^1$H NMR of coumarin groups (270 MHz, CDCl$_3$, ppm) $\delta$4.69 (2H, doublet), 6.26 (1H, doublet, J=9.3 Hz), 6.79 (1H, doublet, J=2.4 Hz), 6.87 (1H, quartet, J=2.4, and 8.3 Hz), 7.39 (1H, doublet, J=8.3 Hz), 7.62 (1H, doublet, J=9.3 Hz).

Assuming 100% conversion of the hydroxyl endgroups of the liquid absorbable copolymers into coumarin esters, UV spectroscopy could be used to estimate the equivalent weight of the resulting photocurable polymer and subsequently its molecular weight by simple multiplication by the number of branches. A typical measurement was conducted as follows. 10 miligrams of coumarin ester endcapped copolymer was dissolved in 40.0 mL of DMF, and UV spectrum measured. The coumarin content was calculated from the value of UV absorption [$\epsilon_{max}$ of coumarin=1.35×10$^4$]. For example, the equivalent weight of the endcapped copolymer of example 4 was 3.65×10$^{-4}$ mol/g.

The polymerization and endcapping results are summarized in Table 1.Table 1. Polymers and Endcapping Results

| Exp | Initiator | Molar Fraction[a] | N[b] | Molar Composition (CL:TMC) | MW[c] | OH value (mol/g)[d] | MW[e] |
|---|---|---|---|---|---|---|---|
| A | $CH_2(CH_2OH)_2$ | 0.076 | 2 | 49/50 | 3200 | | |
| B | PEG1000 | 0.076 | 2 | 50/50 | 4700 | $3.40 \times 10^{-4}$ | 5800 |
| C | $CH_3CH_2C(CH_2OH)_3$ | 0.152 | 3 | 51/49 | 2900 | $8.34 \times 10^{-4}$ | 3600 |
| D | $CH_3CH_2C(CH_2OH)_3$ | 0.114 | 3 | 50/50 | 4200 | $5.88 \times 10^{-4}$ | 5100 |
| E | $CH_3CH_2C(CH_2OH)_3$ | 0.076 | 3 | 50/50 | 8100 | $3.22 \times 10^{-4}$ | 9300 |
| F | $CH_3CH_2C(CH_2OH)_3$ | 0.049 | 3 | 50/50 | 12400 | $3.00 \times 10^{-4}$ | 10000 |
| G | $CH_3CH_2C(CH_2OH)_3$ | 0.076 | 3 | 59/41 | 6100 | $3.52 \times 10^{-4}$ | 8500 |
| H | $CH_3CH_2C(CH_2OH)_3$ | 0.076 | 3 | 39/61 | 5900 | $3.55 \times 10^{-4}$ | 8500 |
| I | $CH_3CH_2C(CH_2OH)_3$ + PEG600 (1:1) | 0.075 | 3/2 | 50/50 | 5400 | | |
| J | $CH_3CH_2C(CH_2OH)_3$ | 0.076 | 3 | 0/100 | 4800 | $5.77 \times 10^{-4}$ | 5200 |
| K | $C(CH_2OH)_4$ | 0.260 | 4 | 49/51 | 2800 | $1.26 \times 10^{-3}$ | 3200 |
| L | $C(CH_2OH)_4$ | 0.152 | 4 | 49/51 | 5300 | $7.90 \times 10^{-4}$ | 5100 |
| M | $C(CH_2OH)_4$ | 0.076 | 4 | 50/50 | 13800 | $3.39 \times 10^{-4}$ | 11800 |
| N | $C(CH_2OH)_4$ | 0.152 | 4 | 0/100 | 4200 | $8.00 \times 10^{-4}$ | 5000 |
| O | $C(CH_2OH)_4$ | 0.152 | 4 | 27/73 | 4800 | $8.04 \times 10^{-4}$ | 5000 |
| P | $C(CH_2OH)_4$ | 0.152 | 4 | 7/93 | 4600 | $8.00 \times 10^{-4}$ | 5000 |
| Q | $C(CH_2OH)_4$ | 0.152 | 4 | 76/24 | 3800 | $8.07 \times 10^{-4}$ | 5000 |
| R | b-PEG[f] | 0.152 | 4 | 50/50 | 7400 | $5.71 \times 10^{-4}$ | 7000 |

[a]Molar fraction of OH group per total molecular concentration.
[b]Multifunctionality of initiator.
[c]Number-average molecular weight determined by GPC (PEO Standard).
[d]The quantities of coumarin moieties of coumarinated copolymer were calculated by UV measurement.
[e]Molecular weight calculated by coumarin content.
[f]Branched-PEG (diglycerol polyoxyethylene glycol ether) (M.W. 2,040) purchased from Shearwater, Inc.;

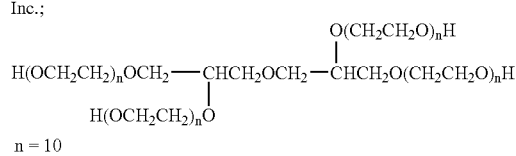

$n = 10$

EXAMPLE 6
Network Formation by Irradiation

The typical procedure for photogelation of these coumarin ester endcapped, liquid absorbable polymers is discussed below.

40 milligrams of coumarin end-capped polymer was dissolved in 1.00 mL of dichloromethane, 150 μL of this solution was dropped on a cover glass (diameter 14.5 mm), and then the dichloromethane was removed under reduced pressure to prepare a thin film having a thickness of 0.03 mm. The film was irradiated with ultraviolet light (Hg—Xe lamp) of varying intensity and time. The polymeric network or gel that formed was washed with dichloromethane and dried under reduced pressure to constant weight. The gel was weighed and gel yield calculated. FIG. 1 shows a plot of the gel yield as a function of time for three ultraviolet radiation intensities for polymer E in Table 1. Clearly, the rate of photocuring is dependent on the ultraviolet intensity, but at approximately 100 mW/cm³, gelation is completed in less than two minutes at this thickness.

EXAMPLE 7
In vitro Absorption Rates of Photocured Films

Figure 2:
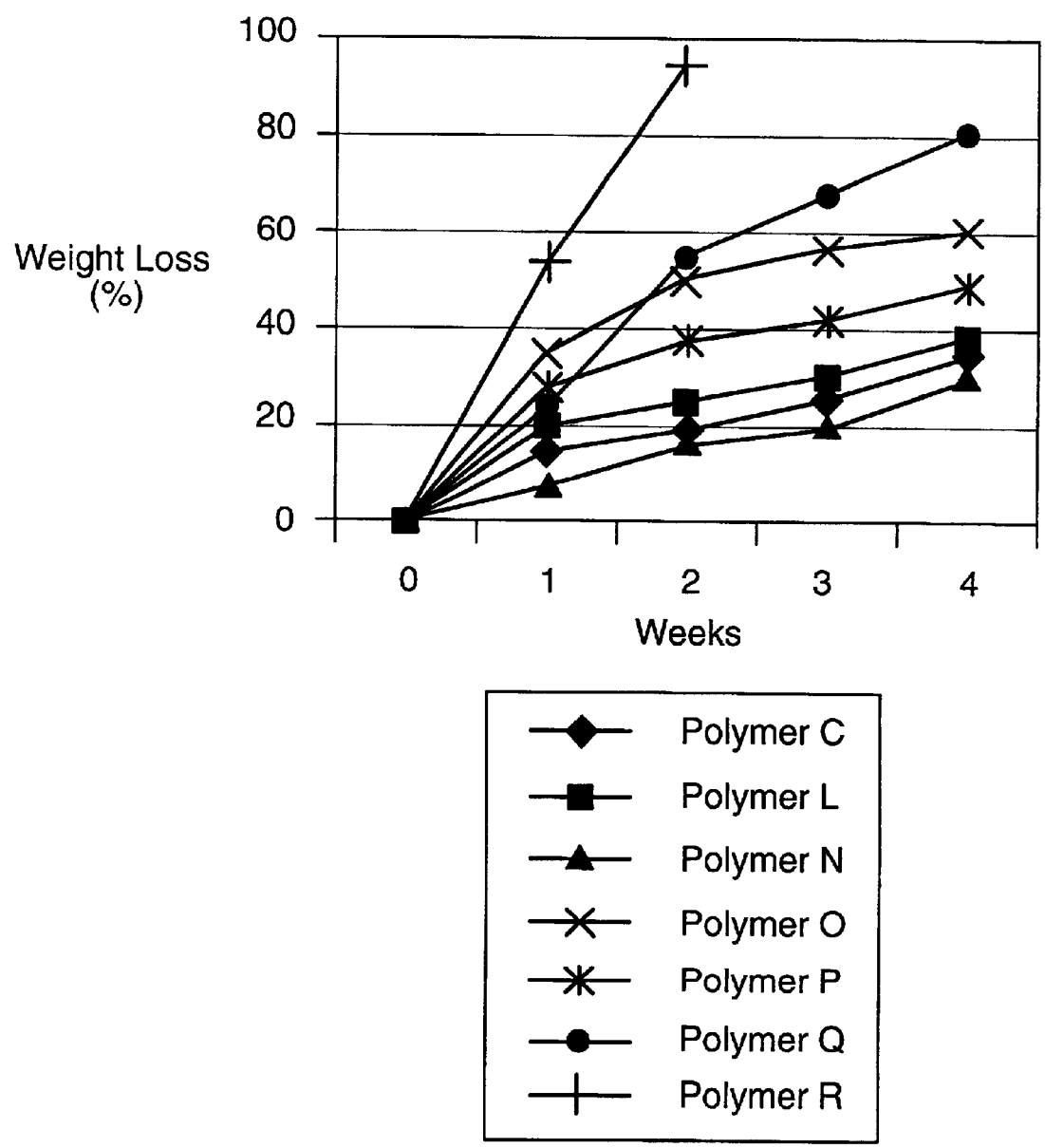
FIG. 2 is the graph plotting the weight loss of a crosslinked film as a function of the time immersed in phosphate buffered saline pH 7.4 at 37° C.

Thin films such as the one described in Example 6 made from coumarin ester endcapped polymers C, L, N, O, P, Q, and R, in Table 1 were immersed in phosphate buffered saline pH 7.4 at 37° C. The films were removed and weighed once a week. The PBS buffer was also changed weekly. The absorption profiles of these films is plotted in FIG. 2. It is clearly evident from this graph that the absorption of these polymeric networks can be controlled by their overall chemical composition. As expected, the material containing some poly(ethylene glycol) degraded most rapidly.

EXAMPLE 8
Microparticle Formation

Coumarin endcapped, liquid copolymer L of Table 1 was dissolved in a mixture of dioxane and water and poured into a beaker containing liquid paraffin containing 0.2% sorbitan trioleate and a magnetic stirring bar. The mixture was stirred at 200 rpm's and irradiated with ultraviolet light for thirty minutes at an intensity of 10.8 mW/cm². The microparticles were isolated by filtration and washed thoroughly with n-hexane. The microspheres contained about 5% water.

The same experiment was repeated using coumarin endcapped, liquid copolymer R of Table 1. In this case, the resulting microsheres contained about 10% water which is expected based on the increased hydrophilicity of this material due to the incorporation of poly(ethylene glycol) in the network.

EXAMPLE 9
Surface Modification

Figure 3:
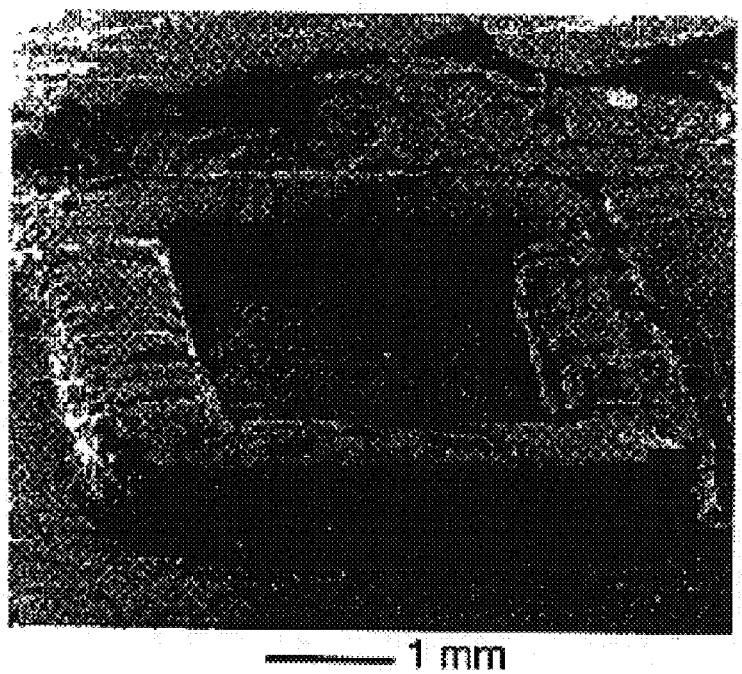
FIG. 3 is the scanning electron micrograph of a square made by using coumarin ester endcapped, liquid absorbable polymers as a photoresist material.

On a primed cover glass, a thin layer of coumarin ester endcapped liquid absorbable polymer L from Table 1 was applied. The primer was a thin layer of poly[2-(7-coumaryloxy)ethyl methacrylate-co-dimethyl acrylamide] that was subsequently irradiated to form a highly crosslinked, coumarinated surface. A computer controlled ultraviolet pen light (Hg—Xe lamp/light width=1.0 mm) moving at 10 microns per second irradiated the substrate in the shape of a square. After ten cycles, the uncured liquid polymer was dissolved away using dichloromethane, and the substrate dried. As shown in FIG. 3, upon inspection using scanning electron microscopy, a square shape was observed on the surface; its line width was about 0.9 mm and its height above the substrate's surface was approximately 400 microns. This experiment demonstrates the use of the coumarin ester endcapped, liquid absorbable polymers as surface coatings, either as a uniform coating or one with specific topology incorporated on the surface. In the field of implantable medical devices, there are advantages to presenting the right surface topology to the surrounding tissue to reduce inflammation and to encourage cellular attachment to the device; this cellular attachment is especially important when the device is a tissue engineering scaffold. In addition, it has been shown that these same coumarin ester endcapped materials can be used as a resin in a stereolithography apparatus.

We claim:

1. A method of forming medical implants, comprising:
    irradiating in vivo a fluid prepolymer comprising a polymer prepared from at least one lactone monomer selected from the group consisting of $\epsilon$-caprolactone, trimethylene carbonate, glycolide, L-lactide, D-lactide, DL-lactide, p-dioxanone, 5,5-dimethyl-1,3-dioxan-2-one, 1,4-dioxepan-2-one and 1,5-dioxepan-2-one, said prepolymer being a liquid at 65° C. or at a lower temperature and comprising coumarin ester endgroups, wherein the inherent viscosity of the polymer is between about 0.05 dL/g and about 0.8 dL/g as determined in 0.1 g/dL solution of hexafluoroisopropanol at 25° C.

2. The method of claim 1 wherein the implant is selected from the group consisting of an adhesion prevention barrier, a tissue bulking agent, a defect filler, a surgical sealant and a surgical pledget.

3. The method of claim 1 wherein said fluid prepolymer further comprises at least one bioactive compound in a therapeutically effective amount.

4. The method of claim 3 wherein the implant is selected from the group consisting of an adhesion prevention barrier, a tissue bulking agent, a defect filler, a surgical sealant and a surgical pledget.

* * * * *